United States Patent
Peters et al.

(10) Patent No.: US 7,855,208 B2
(45) Date of Patent: Dec. 21, 2010

(54) 3, 9-DIAZABICYCLO(3.3.1)NON-3-YL-ARYL METHANONE DERIVATIVES AS NICOTINIC ACETYLCHOLINE RECEPTOR AGONISTS

(75) Inventors: Dan Peters, Malmö (SE); Daniel B. Timmermann, Herlev (DK); Gunnar M. Olsen, Smørum (DK); Elsebet Ostergaard Nielsen, København K (DK)

(73) Assignee: NeuroSearch A/S, Ballerup (DK)

( * ) Notice: Subject to any disclaimer, the term of this patent is extended or adjusted under 35 U.S.C. 154(b) by 315 days.

(21) Appl. No.: 12/160,567

(22) PCT Filed: Feb. 13, 2007

(86) PCT No.: PCT/EP2007/051397

§ 371 (c)(1),
(2), (4) Date: Jul. 10, 2008

(87) PCT Pub. No.: WO2007/093601

PCT Pub. Date: Aug. 23, 2007

(65) Prior Publication Data

US 2010/0234384 A1    Sep. 16, 2010

(30) Foreign Application Priority Data

Feb. 14, 2006  (DK) ............................... 2006 00211

(51) Int. Cl.
*A01N 43/58* (2006.01)
*A01N 43/60* (2006.01)
*A61K 31/50* (2006.01)
*A61K 31/495* (2006.01)
*C07D 241/36* (2006.01)

(52) U.S. Cl. ........................ 514/249; 544/349
(58) Field of Classification Search ............... None
See application file for complete search history.

(56) References Cited

U.S. PATENT DOCUMENTS

| | | | |
|---|---|---|---|
| 3,293,251 A | 12/1966 | Cignarolla et al. | |
| 2003/0225268 A1 | 12/2003 | Bunnelle et al. | |
| 2005/0137226 A1 | 6/2005 | Ji et al. | |
| 2005/0250808 A1 | 11/2005 | Xie et al. | |

FOREIGN PATENT DOCUMENTS

| WO | WO-98/54182 A1 | 12/1998 |
|---|---|---|
| WO | WO-00/44755 A1 | 8/2000 |
| WO | WO-2004/016616 A1 | 2/2004 |
| WO | WO-2004/016617 A1 | 2/2004 |
| WO | WO-2004/022556 A1 | 3/2004 |
| WO | WO-2004/043960 A1 | 5/2004 |
| WO | WO-2006/005608 A1 | 1/2006 |
| WO | WO-2006/040352 A1 | 4/2006 |
| WO | WO-2006/04571 A1 | 5/2006 |
| WO | WO-2006/045716 A1 | 5/2006 |
| WO | WO-2006/058879 A1 | 6/2006 |
| WO | WO-2006/087306 A2 | 8/2006 |
| WO | WO-2007/065892 A1 | 6/2007 |

OTHER PUBLICATIONS

Liu and Zhao, "Nicotine attenuates β-amyloid peptide-induced neurotoxicity, free radical and calcium accumulation in hippocampal neuronal cultures" British Journal of Pharmacology, vol. 141, pp. 746-754 (2004).*
Giunta et al, "Galantamine and nicotine have a synergistic effect on inhibition of microglial activation induced by HIV gp120" Brain Research Bulletin, vol. 64, pp. 165-170 (2004).*
Suto and Zacharias, "Neuronal nicotinic acetylcholine receptors as drug targets" Expert Opinion on Therapeutic Targets, vol. 8(2), pp. 61-64 (2004).*
Tariq et al, "Neuroprotective effect of nicotine against 3-nitropropionic acid (3-NP)-induced experimental Huntington's disease in rats" Brain Research Bulletin, vol. 67, pp. 161-168 (2005).*
Hernandez and Terry, Jr., "Repeated Nicotine Exposure in Rats: Effects on Memory Function, Cholinergic Markers and Nerve Growth Factor" Neuroscience, vol. 130, pp. 997-1012 (2006).*
Gotti et al, "Brain Neuronal Nicotinic Receptors as New Targets for Drug Discovery" Current Pharmaceutical Design, vol. 12, pp. 407-428 (2006).*

* cited by examiner

*Primary Examiner*—Zachary Tucker
(74) *Attorney, Agent, or Firm*—Birch, Stewart, Kolasch & Birch, LLP

(57) ABSTRACT

This invention relates to novel diazabicyclic aryl derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

9 Claims, No Drawings

3,9-DIAZABICYCLO(3.3.1)NON-3-YL-ARYL METHANONE DERIVATIVES AS NICOTINIC ACETYLCHOLINE RECEPTOR AGONISTS

TECHNICAL FIELD

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel diaza-bicyclo-alkane derivatives. The diaza-bicyclo-alkane derivatives of the invention may be represented by the general Formula I

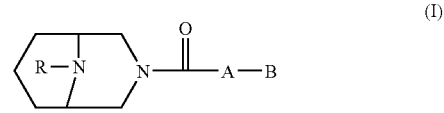

an isomer thereof or a mixture of its isomers, or a pharmaceutically acceptable salt thereof, wherein R represents hydrogen or alkyl;

A represents an aromatic monocyclic or bicyclic carbocyclic or heterocyclic group; and B represents aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamide.

In its second aspect the invention provides pharmaceutical compositions comprising a therapeutically effective amount of the diaza-bicyclo-alkane derivative of the invention, or a pharmaceutically-acceptable addition salt thereof, together with at least one pharmaceutically-acceptable carrier or diluent.

In a further aspect the invention relates to the use of the diaza-bicyclo-alkane derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diaza-bicyclo-alkane derivative of the invention.

Other objects of the invention will be apparent to the person skilled in the art from the following detailed description and examples.

DETAILED DISCLOSURE OF THE INVENTION

Diaza-bicyclo-alkene Derivatives

In a first aspect novel diaza-bicyclo-alkane derivatives are provided. The diaza-bicyclo-alkane derivatives of the invention may be represented by the general Formula I

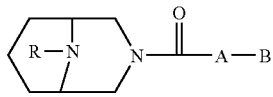

(I)

an isomer thereof or a mixture of its isomers, or a pharmaceutically acceptable salt thereof, wherein R represents hydrogen or alkyl;

A represents an aromatic monocyclic or bicyclic carbocyclic or heterocyclic group; and B represents aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

In a preferred embodiment the diaza-bicyclo-alkane derivative of the invention is a compound of Formula I wherein R' represents hydrogen or alkyl.

In a more preferred embodiment R' represents alkyl.

In an even more preferred embodiment R' represents methyl or ethyl.

In another preferred embodiment the diaza-bicyclo-alkane derivative of the invention is a compound of Formula I wherein A represents an aromatic monocyclic or bicyclic carbocyclic or heterocyclic group.

In a more preferred embodiment A represents an aromatic group selected from phenyl, furanyl and benzo[b]furanyl.

In an even more preferred embodiment A represents an aromatic monocyclic group selected from phen-1,4-diyl, furan-2,5-diyl and benzo[b]furan-1-yl.

In a still more preferred embodiment A represents an aromatic bicyclic heterocyclic group selected from indolyl, benzo[b]furanyl, benzo[b]thienyl, and benzimidazolyl.

In a yet more preferred embodiment A represents benzo[b]furanyl.

In a further preferred embodiment A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl and triazinyl.

In a still further preferred embodiment A represents an aromatic heterocyclic group selected from furanyl, in particular furan-2,3-diyl, furan-2,4-diyl and furan-2,5-diyl; thienyl, in particular thien-2,3-diyl, thien-2,4-diyl and thien-2,5-diyl; pyrrolyl, in particular pyrrol-2,3-diyl, pyrrol-2,4-diyl and pyrrol-2,5-diyl; oxazolyl, in particular oxazol-2,4-diyl and oxazol-2,5-diyl; thiazolyl, in particular thiazol-2,4-diyl and thiazol-2,5-diyl; imidazolyl, in particular imidazol-2,4-diyl and imidazol-2,5-diyl; isoxazolyl, in particular isoxazol-3,4-diyl and isoxazol-3,5-diyl; isothiazolyl, in particular isothiazol-3,4-diyl and isothiazol-3,5-diyl; pyridyl, in particular pyrid-2,4-diyl, pyrid-2,5-diyl and pyrid-2,6-diyl; pyridazinyl, in particular pyridazin-3,5-diyl and pyridazin-3,6-diyl; pyrimidinyl, in particular pyrimidin-2,4-diyl and pyrimidin-2,5-diyl; pyrazinyl in particular pyrazin-2,5-diyl and pyrazin-2,6-diyl.

In a still further preferred embodiment A represents furanyl, in particular furan-2,3-diyl, furan-2,4-diyl or furan-2,5-diyl; oxazolyl, in particular oxazol-2,4-diyl or oxazol-2,5-diyl; or isoxazolyl, in particular isoxazol-3,4-diyl or isoxazol-3,5-diyl.

In a still further preferred embodiment A represents furanyl.

In a most preferred embodiment A represents furan-2,5-diyl.

In a third preferred embodiment the diaza-bicyclo-alkane derivative of the invention is a compound of Formula I wherein B represents aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

In a more preferred embodiment B represents aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

In an even more preferred embodiment B represents phenyl or naphthyl, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

In a still more preferred embodiment B represents phenyl, which carbocyclic group is optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido and N-alkyl-ureido.

In a yet more preferred embodiment B represents phenyl, which carbocyclic group is optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, ureido and N-alkyl-ureido.

In a further more preferred embodiment B represents phenyl optionally substituted with amino, nitro, alkyl-carbonyl-amino, phenyl-carbonyl-amino, ureido or N-alkyl-ureido.

In a still further more preferred embodiment B represents phenyl optionally substituted with amino, nitro, alkyl-carbonyl-amino, ureido or N-alkyl-ureido.

In a most preferred embodiment the diaza-bicyclo-alkane derivative of the invention is (9-Methyl-3,9-diaza-bicyclo[3.3.1]non-3-yl)-[5-(4-nitro-phenyl)-furan-2-yl]-methanone;

[5-(4-Amino-phenyl)-furan-2-yl]-(9-methyl-3,9-diaza-bicyclo[3.3.1]non-3-yl)-methanone;

N-{4-[5-(9-Methyl-3,9-diaza-bicyclo[3.3.1]nonane-3-carbonyl)-furan-2-yl]-phenyl}-benzamide;

1-Ethyl-3-{4-[5-(9-methyl-3,9-diaza-bicyclo[3.3.1]nonane-3-carbonyl)-furan-2-yl]-phenyl}-urea; or N-{4-[5-(9-Methyl-3,9-diaza-bicyclo[3.3.1]nonane-3-carbonyl)-furan-2-yl]-phenyl}-acetamide;

or an isomer or a mixture of its isomers, or a pharmaceutically acceptable salt thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O-" group, wherein alkyl is as defined above. Examples of preferred alkoxy groups of the invention include methoxy and ethoxy.

In the context of this invention a cyano-alkyl group designates an alkyl group substituted with —CN, wherein alkyl is as defined above.

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined above, which alkyl group is substituted one or more times with halo. Preferred haloalkyl groups of the invention include trihalomethyl, preferably trifluoromethyl.

In the context of this invention a haloalkoxy group designates an alkoxy group as defined herein, which alkoxy group is substituted one or more times with halo. Preferred haloalkoxy groups of the invention include trihalomethoxy, preferably trifluoromethoxy.

In the context of this invention an alkyl-carbonyl-amino group designates an "alkyl-CO—NH-" group, wherein alkyl is as defined above. Preferred alkyl-carbonyl-amino groups of the invention include acetamido.

In the context of this invention an N-alkyl-ureido group designates an "alkyl-NH—(CO)—NH-group", wherein alkyl is as defined above. Preferred N-alkyl-ureido groups of the invention include the N-methyl-, the N-ethyl- and the N-propyl-ureido groups.

In the context of this invention an N-alkyl-amido group designates an "alkyl-NH—(CO)-group", wherein alkyl is as defined above. Preferred N-alkyl-amido groups of the invention include the N-methyl-, the N-ethyl- and the N-propyl-amido groups.

In the context of this invention an N,N-dialkyl-amido group designates an "(alkyl)$_2$-N—(CO)-group", wherein alkyl is as defined above. Preferred N,N-dialkyl-amido groups of the invention include the N,N-dimethyl-, the N,N-diethyl- and the N,N-dipropyl-amido groups.

In the context of this invention an N-alkyl-sulfonamido group designates an "alkyl-NH-(SO$_2$)-group", wherein alkyl is as defined above. Preferred N-alkyl-sulfonamido groups of the invention include the N-methyl-, the N-ethyl- and the N-propyl-sulfonamido groups.

In the context of this invention an N,N-dialkyl-sulfonamido group designates an "(alkyl)$_2$-N—(SO$_2$)-group", wherein alkyl is as defined above. Preferred N,N-dialkyl-sulfonamido groups of the invention include the N,N-dimethyl-, the N,N-diethyl- and the N,N-dipropyl-sulfonamido groups.

In the context of this invention an aromatic monocyclic or bicyclic carbocyclic designates an aromatic carbocyclic group holding carbon only as ring atom (i.e. an aryl group). Preferred aryl groups of the invention include phenyl, indenyl, naphthyl, azulenyl, fluorenyl, and anthracenyl. In a most preferred embodiment an aryl group of the invention is phenyl.

In the context of this invention an aromatic monocyclic or bicyclic heterocyclic group designates a mono- or bicyclic compound, which holds one or more heteroatoms in its ring structure. The term "bi-heterocyclic groups" includes benzo-fused five- and six-membered heterocyclic rings containing one or more heteroatoms. Preferred heteroatoms include nitrogen (N), oxygen (O), and sulphur (S).

Preferred 5-6 membered heteroaryl groups of the invention include furanyl, in particular furan-2- or 3-yl; thienyl, in particular thien-2- or 3-yl; selenophenyl, in particular selenophen-2- or 3-yl; pyrrolyl(azolyl), in particular pyrrol-2- or 3-yl; oxazolyl, in particular oxazol-2,4- or 5-yl; thiazolyl, in particular thiazol-2,4- or 5-yl; imidazolyl, in particular imidazol-2- or 4-yl; pyrazolyl, in particular pyrazol-3- or 4-yl; isoxazolyl, in particular isoxazol-3,4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4- or 5-yl, or 1,3,4-thiadiazol-2-yl; pyridyl, in particular pyrid-2-, 3- or 4-yl; pyridazinyl, in particular pyridazin-3- or 4-yl; pyrimidinyl, in particular pyrimidin-2-, 4- or 5-yl; pyrazinyl, in particular pyrazin-2- or 3-yl; and triazinyl, in particular 1,2,4- or 1,3,5-triazinyl.

More preferred 5 membered heteroaryl groups of the invention include furanyl, in particular furan-2- or 3-yl; thienyl, in particular thien-2- or 3-yl; pyrrolyl (azolyl), in particular pyrrol-2- or 3-yl; oxazolyl, in particular oxazol-2,4- or 5-yl; thiazolyl, in particular thiazol-2,4- or 5-yl; isoxazolyl, in particular isoxazol-3,4- or 5-yl; isothiazolyl, in particular isothiazol-3-, 4- or 5-yl; and thiadiazolyl, in particular 1,2,3-thiadiazol-4- or 5-yl, or 1,3,4-thiadiazol-2-yl.

Most preferred 5 membered heteroaryl groups of the invention include furanyl, in particular furan-2- or 3-yl; and thienyl, in particular thien-2- or 3-yl.

More preferred 6 membered heteroaryl groups of the invention include pyridyl, in particular pyrid-2-, 3- or 4-yl; and pyrazinyl, in particular pyrazin-2- or 3-yl.

Pharmaceutically Acceptable Salts

The diazabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Additional examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Isomers

It will be appreciated by those skilled in the art that the compounds of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & When S in "*Enantiomers, Racemates, and Resolutions*", John Wiley and Sons, New York (1981).

Optical active compounds can also be prepared from optical active starting materials.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Producing Diazabicyclic Aryl Derivatives

The diazabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the present invention may be useful for the treatment, prevention or alleviation of a cognitive disorder, learning deficit, memory deficits and dysfunction, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention may be useful for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the compounds of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the compounds of the invention may be useful for the treatment, prevention or alleviation of a neurodegenerative disorder, transient anoxia, or induced neuro-degeneration.

In a yet more preferred embodiment the compounds of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the compounds of the invention may be useful for the treatment, prevention or alleviation of diabetic neuropathy, schizophrenia, cognitive or attentional deficits related to schizophrenia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 μM.

Pharmaceutical Compositions

In another aspect the invention provides novel pharmaceutical compositions comprising a therapeutically effective amount of diazabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the to same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result cart, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an diazabicyclic aryl derivative of the invention.

In the context of this invention the term "treatment" covers treatment, prevention, prophylaxis or alleviation, and the term "disease" covers illnesses, diseases, disorders and conditions related to the disease in question.

The preferred medical indications contemplated according to the invention are those stated above.

It is at present contemplated that suitable dosage ranges are within 0.1 to 1000 milligrams daily, preferably 10 to 500 milligrams daily, and more preferred of from 30 to 100 milligrams daily, dependent as usual upon the exact mode of administration, form in which administered, the indication toward which the administration is directed, the subject involved, the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulphate was used as drying agent in the workup-procedures and solvents were evaporated under reduced pressure.

Method A (9-Methyl-3,9-diaza-bicyclo[3.3.1]non-3-yl)-[5-(4-nitro-phenyl)-furan-2-yl]-methanone hydrochloric acid salt (Compound A1)

9-Methyl-3,9-diaza-bicyclo[3.3.1]nonane (2.0 g, 14.3 mmol), 5-(4-nitro-phenyl)-furan-2-carboxylic acid chloride (3.59 g, 14.3 mmol) and 1,2-dimethoxyethane (40 ml) was stirred at room temperature for 15 hours. The product was filtered and was purified by washing with 1,2-dimethoxyethane (100 ml). Yield 5.24 g (94%). Mp. 263° C.

Method B

[5-(4-Amino-phenyl)-furan-2-yl]-9-methyl-3,9-diaza-bicyclo[3.3.1]non-3-yl)-methanone free base (Compound B1)

(9-Methyl-3,9-diaza-bicyclo[3.3.1]non-3-yl)-[5-(4-nitro-phenyl)-furan-2-yl]-methanone hydrochloric acid (5.1 g, 13.0 mmol) and palladium (5% on calcium carbonate, 500 mg) poisoned with lead was stirred under an atmosphere of hydrogen. The mixture was evaporated. The crude mixture was purified by silica gel column chromatography by using a mixture of dichloromethane, methanol and aqueous ammonia (9:1+1%). Yield 2.4 g (57%). Mp. 147-149° C.

Method C

N-{4-[5-(9-Methyl-3,9-diaza-bicyclo[3.3.1]nonane-3-carbonyl)-furan-2-yl]-phenyl}-benzamide fumaric acid salt (Compound C1)

Benzoyl chloride (0.19 g, 1.38 mmol) was added to a mixture of [5-(4-amino-phenyl)-furan-2-yl]-(9-methyl-3,9-diaza-bicyclo[3.3.1]non-3-yl)-methanone free base (0.30 g, 0.92 mmol) in dichloromethane (20 ml) at 0° C. The mixture was allowed to stir at room temperature overnight. Aqueous sodium hydroxide (20 ml, 1 M) was added followed by extraction by dichloromethane (3×20 ml). The mixture was evaporated. The crude mixture was purified by silica gel column chromatography by using a mixture of dichloromethane, methanol and aqueous ammonia (9:1+1%). Yield 370 mg (93%). The corresponding salt was obtained by addition of a diethyl ether and methanol mixture (9:1) saturated with fumaric acid. Mp. 246-252° C.

1-Ethyl-3-{4-[5-(9-methyl-3,9-diaza-bicyclo[3.3.1]nonane-3-carbonyl)-furan-2-yl]-phenyl}-urea fumaric acid salt (Compound C2)

Was prepared by Method C from [5-(4-amino-phenyl)-furan-2-yl]-(9-methyl-3,9-diaza-bicyclo[3.3.1]non-3-yl)-methanone free base and ethylisocyanate using −50° C. as mixing temperature. Mp. 154-161° C.

N-{4-[5-(9-Methyl-3,9-diaza-bicyclo[3.3.1]nonane-3-carbonyl)-furan-2-yl]-phenyl}-acetamide fumaric acid salt (Compound C3)

Was prepared by Method C from [5-(4-amino-phenyl)-furan-2-yl]-(9-methyl-3,9-diaza-bicyclo[3.3.1]non-3-yl)-methanone free base and acetic anhydride using 20° C. as mixing temperature. Mp. 197-229° C.

Example 2

In Vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes.

The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final con-centration) and mixed and incubated for 2×5 hours at 37° C. Non-specific binding is determined using (−)-nicotine (1 mM, final con-centration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an IC$_{SD}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | IC$_{50}$ (μM) |
| B1 | 0.42 |

The invention claimed is:

1. A 3,9-diaza-bicyclo[3.3.1]nonane derivative represented by Formula I

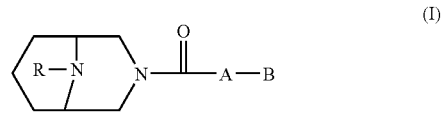

a stereoisomer thereof or a mixture of its stereoisomers, or a pharmaceutically acceptable salt thereof, wherein
R represents hydrogen or alkyl;
A represents an aromatic monocyclic or bicyclic carbocyclic or heterocyclic group; and
B represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

2. The 3,9-diaza-bicyclo[3.3.1]nonane derivative of claim 1, or a pharmaceutically acceptable salt thereof, wherein A represents an aromatic monocyclic group selected from phenyl, furanyl, thienyl, selenophenyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl and triazinyl.

3. The 3,9-diaza-bicyclo[3.3.1]nonane derivative of claim 2, or a pharmaceutically acceptable salt thereof, wherein A represents furan-2,3-diyl, furan-2,4-diyl, furan-2,5-diyl, oxazol-2,4-diyl, oxazol-2,5-diyl, isoxazol-3,4-diyl or isoxazol-3,5-diyl.

4. The 3,9-diaza-bicyclo[3.3.1]nonane derivative of claim 1, or a pharmaceutically acceptable salt thereof, wherein B represents phenyl or naphthyl, which phenyl or naphthyl are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido, N-alkyl-ureido, amido, N-alkyl-amido, N,N-dialkyl-amido, sulfamoyl, sulfonamido, N-alkyl-sulfonamido or N,N-dialkyl-sulfonamido.

5. The 3,9-diaza-bicyclo[3.3.1]nonane derivative of claim 4, or a pharmaceutically acceptable salt thereof, wherein B represents phenyl, which phenyl group is optionally substituted one or two times with substituents selected from the group consisting of alkyl, cycloalkyl, cycloalkyl-alkyl, hydroxy, alkoxy, cyanoalkyl, halo, trihaloalkyl, trihaloalkoxy, cyano, amino, nitro, alkyl-carbonyl-amino, phenyl-carbonyl-amino, ureido and N-alkyl-ureido.

6. The 3,9-diaza-bicyclo[3.3.1]nonane derivative of claim 5, or a pharmaceutically acceptable salt thereof, wherein B represents phenyl optionally substituted with amino, nitro, alkyl-carbonyl-amino, phenyl-carbonyl-amino, ureido or N-alkyl-ureido.

7. The 3,9-diaza-bicyclo[3.3.1]nonane derivative of claim 1, which is
(9-Methyl-3,9-diaza-bicyclo[3.3.1]non-3-yl)-[5-(4-nitro-phenyl)-furan-2-yl]-methanone;
[5-(4-Amino-phenyl)-furan-2-yl]-(9-methyl-3,9-diaza-bicyclo[3.3.1]non-3-yl)-methanone;
N-{4-[5-(9-Methyl-3,9-diaza-bicyclo[3.3.1]nonane-3-carbonyl)-furan-2-yl]-phenyl}-benzamide;
1-Ethyl-3-{4-[5-(9-methyl-3,9-diaza-bicyclo[3.3.1]nonane-3-carbonyl)-furan-2-yl]-phenyl}-urea; or
N-{4-[5-(9-Methyl-3,9-diaza-bicyclo[3.3.1]nonane-3-carbonyl)-furan-2-yl]-phenyl}-acetamide;
or an isomer or a mixture of its isomers, or a pharmaceutically acceptable salt thereof.

8. A pharmaceutical composition comprising:
a therapeutically effective amount of 3,9-diazabicyclo[3.3.1]nonane derivative of claim 1, or a pharmaceutically-acceptable addition salt thereof; and at least one pharmaceutically-acceptable carrier or diluent.

9. A method of treatment or alleviation of a disease or a disorder or a condition selected from the group consisting of memory deficits and dysfunction, Alzheimer's disease, AIDS-dementia, senile dementia, Parkinson's disease, Huntington's disease, and withdrawal symptoms caused by termination of use of tobacco or other nicotine containing products, which method comprises the step of administering to a human or animal subject in need thereof a therapeutically effective amount of a 3,9-diazabicyclo[3.3.1]nonane derivative of claim 1.

* * * * *